United States Patent
Sattler et al.

(10) Patent No.: US 9,504,113 B2
(45) Date of Patent: Nov. 22, 2016

(54) METHOD FOR IMPROVING THE ILLUMINATION OF AN ILLUMINATED AREA

(71) Applicant: Dräger Medical GmbH, Lübeck (DE)

(72) Inventors: Frank Sattler, Lübeck (DE); Livio Fornasiero, Bliestorf (DE); Hartmut Stark, Stockelsdorf (DE)

(73) Assignee: DRÄGERWERK AG & CO. KGaA, Lübeck (DE)

( * ) Notice: Subject to any disclaimer, the term of this patent is extended or adjusted under 35 U.S.C. 154(b) by 0 days.

(21) Appl. No.: 14/416,883

(22) PCT Filed: Jul. 8, 2013

(86) PCT No.: PCT/EP2013/064357
§ 371 (c)(1),
(2) Date: Jan. 23, 2015

(87) PCT Pub. No.: WO2014/016104
PCT Pub. Date: Jan. 30, 2014

(65) Prior Publication Data
US 2015/0208478 A1 Jul. 23, 2015

(30) Foreign Application Priority Data

Jul. 25, 2012 (DE) .................. 10 2012 014 716

(51) Int. Cl.
*H05B 33/08* (2006.01)
*A61B 19/00* (2006.01)
(Continued)

(52) U.S. Cl.
CPC ....... *H05B 33/0848* (2013.01); *A61B 19/5202* (2013.01); *A61B 90/30* (2016.02);
(Continued)

(58) Field of Classification Search
CPC ..................... A61B 19/5202; A61B 2019/521
See application file for complete search history.

(56) References Cited

U.S. PATENT DOCUMENTS 5,193,894 A * 3/1993 Lietar et al. .................. 362/466
6,880,957 B2 4/2005 Walters
(Continued)

FOREIGN PATENT DOCUMENTS

DE         41 22 531 A1    1/1993
DE  10 2008 019 191 A1  10/2009
EP       1 433 998 B1    5/2005

*Primary Examiner* — Douglas W Owens
*Assistant Examiner* — Pedro C Fernandez
(74) *Attorney, Agent, or Firm* — McGlew and Tuttle, P.C.

(57) ABSTRACT

A method is provided for improving the illumination of an illuminated area (100), especially an operating area, of an illuminating device (10) with at least two light modules (20). The method includes the emission of an illuminant characteristic of the light module (20) with a preset amplitude from each light module (20). The reflected amplitudes of all characteristic light types are detected. The detected amplitudes for each light module (20) are compared. The light intensity of at least one light module (20) is varied on the basis of the comparison of the detected amplitudes for each light module (20).

20 Claims, 5 Drawing Sheets

(51) Int. Cl.
  *H05B 37/02* (2006.01)
  *G01J 1/32* (2006.01)
(52) U.S. Cl.
  CPC .......... *H05B 37/02* (2013.01); *H05B 37/0218* (2013.01); *A61B 2019/521* (2013.01); *A61B 2090/309* (2016.02); *G01J 1/32* (2013.01)

(56) References Cited

U.S. PATENT DOCUMENTS

| | | | |
|---|---|---|---|
| 2003/0185009 A1* | 10/2003 | Walters | 362/276 |
| 2004/0129860 A1* | 7/2004 | Thibaud et al. | 250/205 |
| 2005/0219167 A1 | 10/2005 | Hattori et al. | |
| 2008/0290818 A1 | 11/2008 | Fontijn | |
| 2009/0261759 A1* | 10/2009 | Fornasiero | 315/307 |

* cited by examiner

METHOD FOR IMPROVING THE ILLUMINATION OF AN ILLUMINATED AREA

CROSS REFERENCE TO RELATED APPLICATIONS

This application is a United States National Phase Application of International Application PCT/EP2013/064357 filed Jul. 8, 2013 and claims the benefit of priority under 35 U.S.C. §119 of German Patent Application DE 10 2012 014 716.3 filed Jul. 25, 2012, the entire contents of which are incorporated herein by reference.

FIELD OF THE INVENTION

The present invention pertains to a method for improving the illumination of an illuminated area, to an illuminating device for illuminating an illuminated area, as well as to the use of a corresponding illuminating device.

BACKGROUND OF THE INVENTION

Methods for improving illuminated areas and corresponding illuminating devices are, in principle, known. They are used, e.g., to illuminate operating areas during surgical procedures. Such illuminating devices are often provided with at least two light modules, which make the desired illumination available in the direction of the operating area. The operating area thus overlaps, at least in some areas, the illuminated area of such an illuminating device.

When a user of an illuminating device is moving within the illuminated area in order to work there, he will block part of the light emitted by individual light modules by his body parts, e.g., head, back or arm. This blocking leads to shadowing or to a partial shadowing of the illuminated area, so that the brightness of the illuminated area decreases. This will, in turn, lead to worse visibility conditions, which make the work of this person difficult. This is highly disadvantageous in case of use for surgeons and the illumination of operating areas, because high quality of a surgical procedure is associated with good illumination.

It was already proposed, in principle, to detect possible obstacles in the direction of the illuminated area by means of proximity sensors and to correspondingly perform a regulation of the light modules. However, the drawback of this prior-art technique is that the proximity sensors have no essential directional characteristic and the position finding of two or more obstacles in the proximity of the light modules may lead to errors. For example, DE 10 2008 019 191 A1 or EP 1 433 998 B1 show possibilities of illumination with shadow compensation. The consequence of this may be both a slight improvement of illumination and incorrect illumination of the illuminated area.

SUMMARY OF THE INVENTION

An object of the present invention is to at least partially eliminate the above-described drawbacks. In particular, the object of the present invention is to make available a method for improving the illumination of an illuminated area, an illuminating device, as well as a use of an illuminating device, which bring about a reliable reduction of the shadowing of the illuminated area due to an improvement of the illumination in a cost-effective and simple manner.

Features and details that are described in connection with the method according to the present invention are, of course, also applicable in connection with the illuminating device according to the present invention and the use according to the present invention and vice versa, so that reference is and can be mutually made to the individual aspects of the present invention concerning the disclosure.

A method according to the present invention is used to improve the illumination of an illuminated area, especially an operating area, of an illuminating device. Such an illuminating device has at least two light modules, which are each equipped with an illuminating means (an illuminant) A method according to the present invention has the following steps:

Emission of an illuminant characteristic (a light type) of the light module with a preset amplitude of each light module, Detection of the reflected amplitudes of all characteristic light types, Comparison of the detected amplitudes for each light module, and Varying the light intensity, of at least one light module, on the basis of the comparison of the detected amplitudes for each light module.

Separate proximity sensors can be eliminated due to the method according to the present invention. Thus, each light module may have a characteristic light source of its own or a characteristic illuminating means of its own, which emits the characteristic light type. A characteristic light type (characteristic illuminant—characteristic light kind) is defined here as a type of light that can be unambiguously attributed to a light module. Different characteristic parameters of the light may be used here. It is thus possible, e.g., that an unambiguous and hence characteristic wavelength of the light is selected as the characteristic light type for each light module. When using light sources with identical spectral emission characteristics, it is likewise possible to mark the individual light source by filtering out narrow spectral ranges. Other changes, e.g., varying the pulse width modulation, may also be used to characterize the light type with respect to an unambiguous light module.

It is, of course, possible that a separate emitter, especially in the form of an LED, is made available for the emission of the characteristic light type. However, since the light module itself is equipped with an illuminating means (illuminant), the characteristic illuminating (illuminant) means may also be part of the rest of the illuminating means (illuminant) of the light module. It is also possible that the entire light module has only illuminating means (illuminants) that are capable of emitting the characteristic light type.

Consequently, the illuminating device with the at least two light modules is switched on in a method according to the present invention, e.g., to illuminate an illuminated area. Light that illuminates the illuminated area is emitted now by the light modules. At the same time, a characteristic light type, which is detected by a detector or a plurality of detectors with respect to the reflected amplitudes, is now emitted by the light modules. By comparing the detected amplitudes, it can be determined how great the loss is over the course of the path of the light from the light module to the detector. The presence of possible objects in the area between the respective light module and the respective illuminated area can, in turn, be inferred from this loss. The characteristic light type that belongs to a particular light module in an exactly assignable manner, possibly with a reduced reflected amplitude or with an increased reflected amplitude, can be determined by the characteristic light type by means of the detector. It is thus possible not only to generally infer possible objects in the area between the illuminating device and the illuminated area, but rather also to infer the light module in question. It is only as a result of this that it becomes possible to perform an exact regulation of the light module in question or of a light module in question (shadowed or blocked) light module. Contrary to prior-art illuminating devices, regulation can thus take place in a much more specific manner, more accurately and above all more rapidly in order to maintain the illumination of the illuminated area at as constant a level as possible.

If an arm of a surgeon penetrates into the area between the illuminated area and the illuminating device, for example, in case of an illuminating device that is regulated with a method according to the present invention, the illuminated area will be partially blocked. Characteristic light, which is emitted by the respective light modules, falls now from at least some light modules on this arm of the surgeon. It is reflected from the arm and thus travels over a markedly shorter path back to the detector of the individual light module. If an individual light module or each light module is analyzed with a detector of its own, the light module that is blocked by the surgeon's arm will detect an increased amplitude. Due to the blocking with the arm, other detectors, especially detectors of other light modules, will detect a lower amplitude of this characteristic light. The particular light module that is blocked by the surgeon's arm is now determined during the analysis by the comparison of the detected amplitudes. The light intensity of the blocked light module or of the other light modules can then be varied in the manner according to the present invention.

Orthogonally standardized functions are preferably used during the analysis. In particular, the detection of the characteristic light types of all characteristic light types is performed in each detector. Each detector will thus have for the number of light modules a vector as the result, which has the results of the amplitudes of all characteristic light types and correspondingly of all light modules. If the results (vector results) of all detectors are combined, they yield together a matrix, which has a dimension according to the number of light modules. The degree of blocking or a correlation between the blocking object and the corresponding light module can now be obtained by changing or displacing the amplitudes within this matrix. The light intensity of at least one light module can be varied as a result in the manner according to the present invention.

Concerning the comparison of the detected amplitudes, it is possible both to make a comparison with the emitted amplitudes of all characteristic light types for each light module or also a comparison with amplitudes already detected before in time for each light module. It is thus possible to perform a variance comparison with the emitted amplitudes, on the one hand, and also a variance comparison, i.e., a change in the detected amplitudes over time for each light module within the framework of the present invention.

It may be advantageous if the detection of the reflected amplitudes of all characteristic light types is performed in at least two different positions in a method according to the present invention. The arrangement of corresponding detectors leads to the possibility of achieving an improved local resolution concerning the detection of the object and the assignment to a blocked light module. The detection may take place both within and outside the light modules. It is also possible, in principle, that detectors are arranged in the area within or around the illuminated area and hence separately from the light module.

It is likewise possible according to the present invention that the detection of the reflected amplitudes of all characteristic light types is performed with the method in at least two light modules, especially in all light modules. In other words, corresponding detectors are provided in one light module or in all light modules. The position of the detectors and hence also the position of the detection, i.e., of the blocking object, are thus defined even more accurately, or such definition becomes mathematically simpler. Concerning an arrangement of detectors in all light modules, measurement will correspondingly become possible, and this measurement will yield an N-dimensional vector as the result for each detector. N-dimensional is defined here as the reference to a number N of light modules. The vectors are combined in a matrix over all detectors and analyzed in the above-described manner according to the present invention. A change in the blocking situation can thus be analyzed by a comparison of the change in this matrix over time. A comparison may, of course, also be performed with emission amplitudes and correspondingly with an emitted matrix in order to achieve an improvement of the illumination situation of the illuminated area in the manner according to the present invention.

One advantage is likewise achieved by assigning a local blocking of the illuminated area to a light module in the method according to the present invention by the comparison of the detected amplitudes for each light module. This light module may also be called blocked light module. The location of a blocking object can thus be inferred by the local correlation of the emission point of a characteristic light type as well as of the detection point of the characteristic light type. The inference of a correspondingly blocked light module from this location makes it possible to effect a change in the illumination situation in an extremely specific manner. In particular, a specific adaptation of the light intensity of at least one light module, as this will be specified even more closely below, can be performed on the basis of this information on the assignment of the local blocking to a light module.

It is likewise advantageous if the light intensity of at least one light module, which is arranged adjacent to the light module with the assigned blocking, is increased with the method according to the present invention. It is possible, in addition or as an alternative, that the light intensity of the light module with the assigned blocking is reduced. These are two possibilities of how the intensity of at least one light module can be varied. These two possibilities may also be used combined as well as alternatively to one another. If it is recognized that a light module is blocked by an object, e.g., the arm of a surgeon, this object casts a shadow into the illuminated area. To free this illuminated area from this shadow, for example, the light intensities of the adjacent light modules are increased. They consequently additionally assume the illumination of the illuminated area. The blocking is thus superimposed or eliminated, so that the illumination intensity is again increased in the illuminated area or is maintained at an essentially constant level. At the same time or in addition, the light intensity of the shadowed light module can be reduced. The power consumption is thus reduced and the efficiency of the illuminating device is thus improved, on the one hand, and heating of the blocking object (e.g., head) is avoided or markedly reduced, on the other hand In addition, a possibly blinding due to reflection from the blocked object is avoided for the user. By recognizing the blocked light module, it thus becomes possible to improve the illumination situation, on the one hand, and to improve the blinding situation for the user of such a method, on the other hand Further, it is preferred if at least one of the following distinctive features is used as a characteristic light type for each light module in a method according to the present invention:
Wavelength of the light
Dimming frequency of the light
Pulse width modulation
Phase.

Especially the use of pulse width modulation (PWM) is meaningful when using illuminating means (illuminants) in the form of LEDs. The pulse width of the emitted light of the LED is modulated here to generate a certain light intensity. The frequency of modulation may be used as a characteristic parameter in order to make possible an unambiguous assignment to the corresponding light module. The distance between the individual frequencies of pulse width modulation as a characteristic parameter of different light modules is preferably in the range of at least 10 Hz. It can thus be ensured that an unambiguous separation of the detection of the individual characteristic light types can be performed by the detectors. This separation is used to make it possible to unambiguously assign the detected amplitudes of the characteristic light type to the corresponding light module. The characteristic light may be emitted both by one illuminating means (illuminants) and by all illuminating means (illuminants) of the light module. An especially simple possibility of detecting the light flux of an individual illuminating means (illuminant) is to switch the individual illuminating means (illuminants) one after another for defined times/phases and to operate these during the on time with different outputs, which correspond to the respective brightness. A quotient of the driving output to brightness, which is a parameter for the blocking of the illuminating means (illuminant), can then be determined for each illuminating means (illuminant) in the respective phase of activity.

It is likewise advantageous if the characteristic light type has a wavelength in the range of 6 μm to 200 nm with the method according to the present invention. In particular, characteristic light types in the range of wavelengths that are in the range not visible to the human eye are used. It is thus possible that the characteristic light type is formed in the UV range or in the infrared range. This offers the advantage that the visibility conditions in the illuminated area are not compromised by the characteristic light type.

It is likewise advantageous if the characteristic light types have a sinus (sinusoidal) modulation in a method according to the present invention, the phase of sinus modulation being shifted from one light module to the next. A sinus modulation can thus be used, so that the modulated components offset each other in an average over time. This simplifies the control or regulation of the modulation and can preferably already be embodied in the design, so that control or regulation is no longer necessary for characterizing the light type at all.

A variant of a method according to the present invention is advantageous if the comparison of the detected amplitudes is performed several times for each light module and the results obtained over time are likewise compared with one another. This can lead to the monitoring of aging as a secondary function of a method according to the present invention. It is, of course, also possible that the detection of the amplitudes is performed independently from the reflection, as a branching off from the respective corresponding light source or the respective characteristic light module. This branching off can likewise be used to monitor aging or to monitor the emitted amplitude. In particular, a self-diagnosis of the module or of the light module can thus be performed. It is also possible to use such an embodiment to calibrate the method and/or the light module.

The present invention also pertains to an illuminating device for illuminating an illuminated area, having at least two light modules with at least one illuminating means (illuminant) each and with at least one characteristic illuminating means (illuminant) each for emitting a characteristic light type. At least one detector is provided here for the detection of the reflected amplitudes of all characteristic light types and at least one computer is provided for comparing the detected amplitudes. A comparison of the detected amplitudes with the emitted amplitudes of all characteristic light types is preferably performed as well. This illuminating device may have individual light modules, e.g., in the form of an operating lamp. The illuminating means (illuminants) are preferably LEDs. It is, of course, also possible that individual light modules are provided as separate satellites. It is now possible that the orientation of these satellites can be varied by means of a regulating unit. This variation in orientation is brought about especially by means of a motor.

An illuminating device according to the present invention can be perfected such that the computer is designed, further, for varying the light intensity of at least one of the light modules on the basis of the comparison of the detected amplitudes for each light module. An illuminating device according to the present invention is thus preferably used for a method according to the present invention or the computer is designed for carrying out a method according to the present invention. An illuminating device according to the present invention thus offers the same advantages as they were explained in detail with reference to a method according to the present invention.

An illuminating device according to the present invention can be perfected such that at least two detectors are provided, which are arranged especially each in a light module. All light modules are preferably equipped with a separate detector. N detectors are also provided if there are N light modules. Consequently, the detection yields for each detector an N-dimensional vector, as a consequence of this a combination of all vectors during the analysis leads to an N-dimensional matrix. The analysis was already explained in detail further above.

An illuminating device according to the present invention may be perfected such that the at least one characteristic illuminating means (illuminant) is an LED, and the characteristic light type is generated especially by pulse width modulation. The different pulse width modulation is consequently the characteristic feature or the characteristic parameter in this embodiment. The pulse width modulation is preferably based on modulation in the range about a pulse width modulation frequency of 300 Hz. The distances between the individual characteristic pulse width modulations are preferably greater than 10 Hz.

The present invention also pertains to the use of an illuminating device having the features according to the present invention or to a method having the features according to the present invention for a lighting fixture of an operating room. Such a lighting fixture for an operating room can be used by a physician or a surgeon, and the illuminated area is located in the field of the operating area. The illuminating device according to the present invention and a method according to the present invention offer especially great advantages in case of this use.

The present invention will be explained in more detail on the basis of the drawing figures attached. The terms "left"

and "right," "at top" and "at bottom" used here pertain to the orientation of the drawing figures with normal, legible reference numbers.

The present invention shall be explained in more detail on the basis of the following figures and exemplary embodiments, without the present invention being limited to these. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is schematic perspective view showing the embodiment according to

FIG. 2 with a blocking object;

DESCRIPTION OF THE PREFERRED EMBODIMENTS

Figure 1:
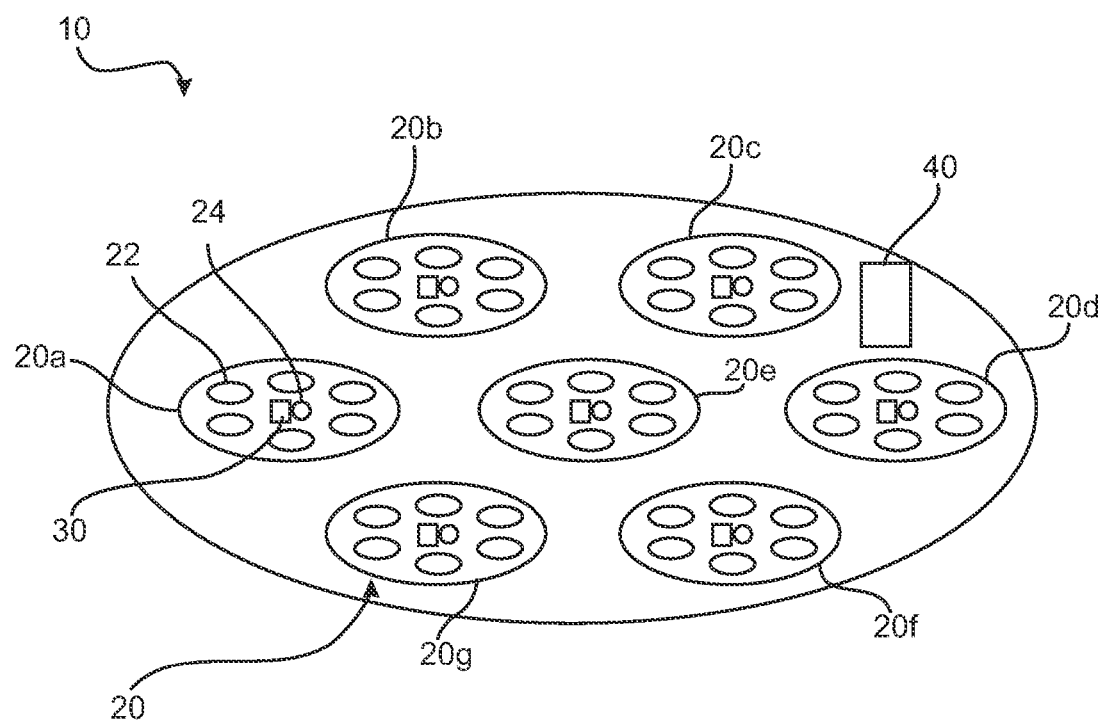
FIG. 1 is schematic perspective view showing a first embodiment of an illuminating device according to the present invention.
Figure 2:
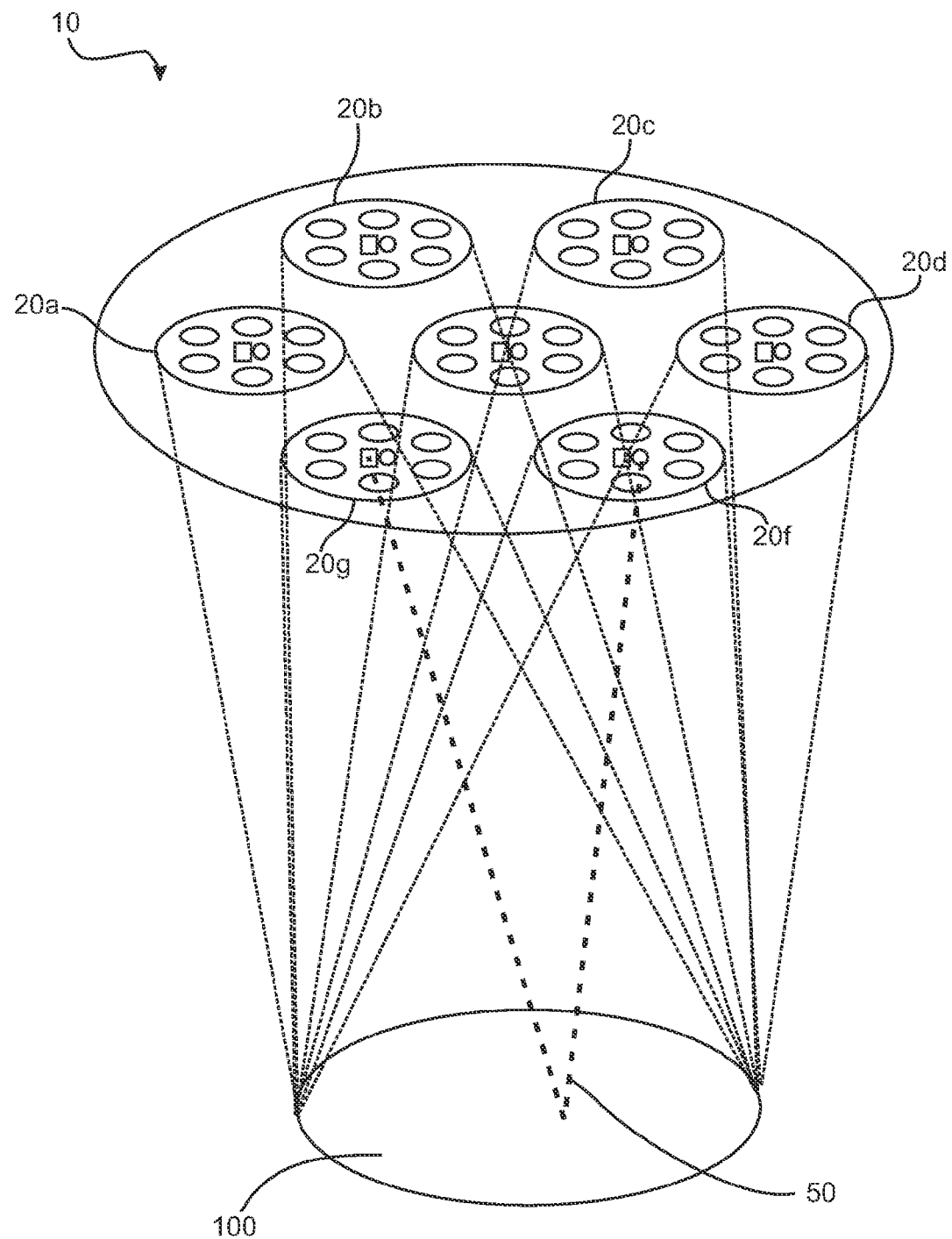
FIG. 2 is schematic perspective view showing an embodiment according to FIG. 1 with the ray paths drawn.
Figure 3:
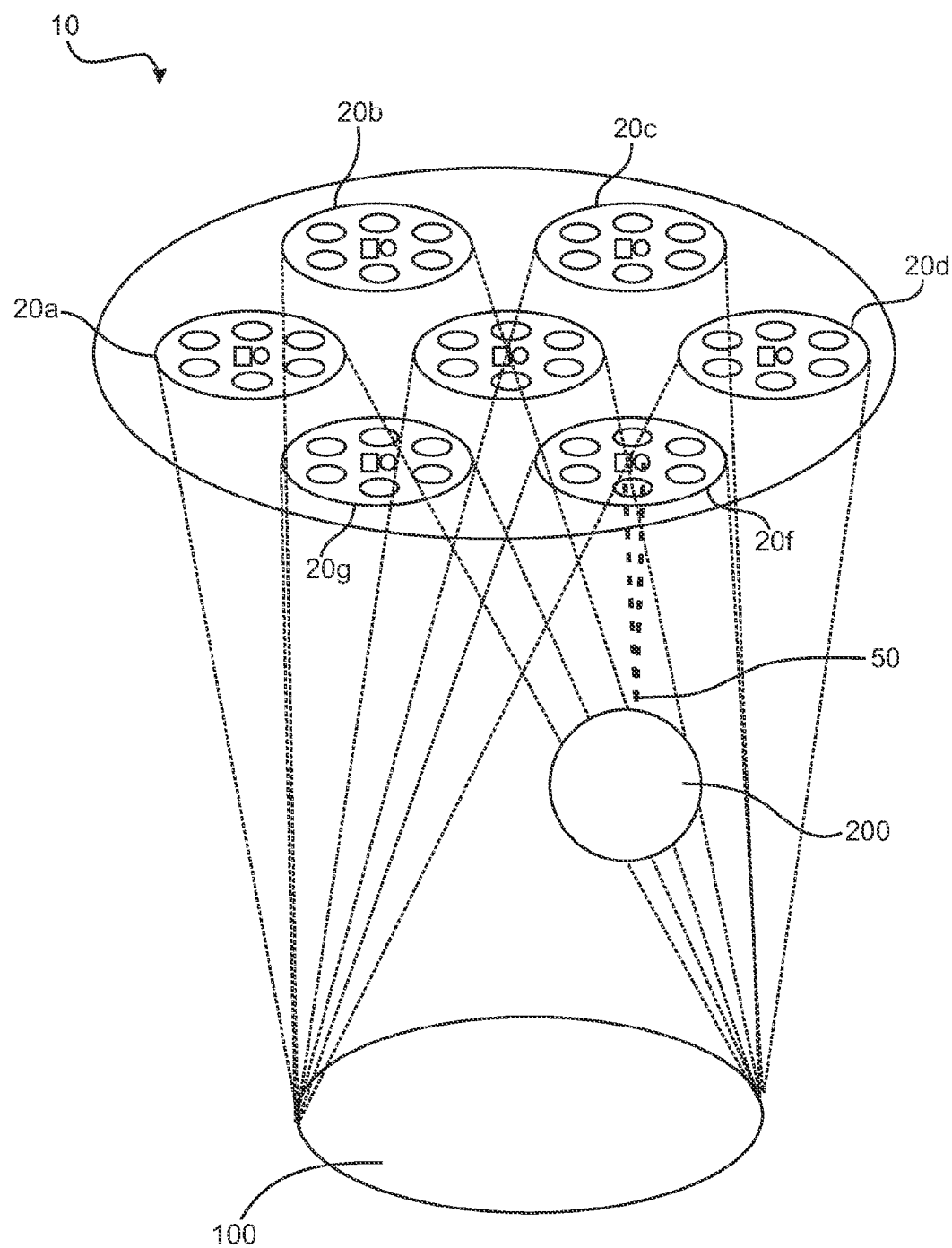

FIGS. 1 through 3 show a first embodiment of an illuminating device 10 according to the present invention. This is provided with a total of seven light modules 20, which are designated each by individual reference numbers 20a, 20b, 20c, 20d, 20e, 20f and 20g. Each of these light modules 20 is provided with a plurality of illuminating means (illuminants) 22, which are especially LEDs. In addition, a characteristic illuminant 24 each is provided for each light module 20. Each light module 20 likewise has a detector 30. The characteristic illuminant 24 is likewise preferably an LED. In addition, a computer 40 is provided, which can carry out a method according to the present invention.

FIGS. 2 and 3 show, in principle, the mode of action of a method according to the present invention with an illuminating device 10 according to the present invention. Based on each light module 20, a characteristic light type is thus generated in each characteristic illuminant 24. This characteristic light type is characteristic especially in respect to the pulse width modulations employed. FIG. 2 shows a situation in which all light modules 20 cast their light onto a common illuminated area 100. This illuminated area 100 is, e.g., the operating area for a surgeon. A first ray path is shown as a detection ray path 50 in FIG. 2, which reaches the illuminated area 100 starting from the light module 20f or the characteristic illuminant 24 located there, it is reflected on said illuminated area 100 and is again detected by all detectors 30, for example, in FIG. 2, especially by the detector 30 of the light module 20g. This detection ray path 50 shall be understood to represent a plurality of ray paths and is shown only as an example in FIG. 2. Thus, a detection ray path 50 extends from each characteristic illuminant 24 to all other detectors 30 as well as to the own detector 30. The ray paths cannot all be shown in the figure because there are a plurality of possible ray paths and the clarity of the figure would be lost.

FIG. 3 shows the situation according to FIG. 2 after an object 200, e.g., the arm of a surgeon, has moved into the area between the illuminated area 100 and the illuminating device 100. This object 200 now casts a shadow on part of the light modules 20 and thus on part of the illuminated area 100. This causes a change in the detection ray path 50, as this is shown in FIG. 2. The ray path 50 is now reflected back onto the own detector 30 of the light module 20f. The detection input of the detection ray path 50 at the detector 30 of the light module 20g, which was still present in FIG. 2, is now missing. The corresponding detected amplitude consequently decreases at the detector 30 of the light module 20g and increases at the detector 30 of the light module 20f. By comparing the individual detected amplitudes over time, a change in the blocking situation can thus be detected due to the shift in the corresponding analysis matrix in the detection. In the situation as shown in FIG. 3, it is possible to unambiguously assign the shadowed object to the light module 20f, because an increased amplitude can be recognized there and a reduced amplitude of the characteristic light type of the light module 20f can be recognized at the other light modules 20a, 20b, 20c, 20d, 20e and 20g.

Figure 4:
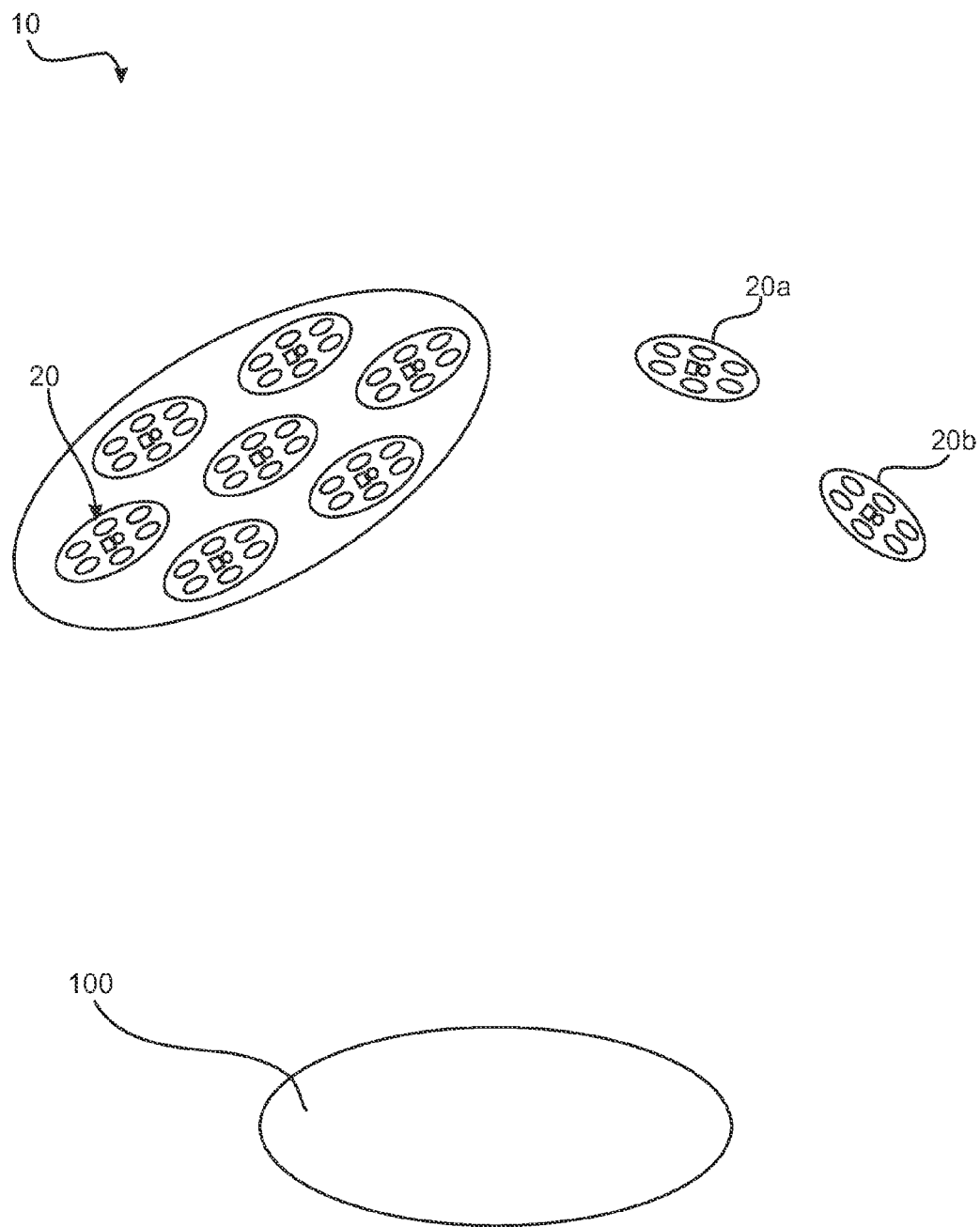
FIG. 4 is schematic perspective view showing another embodiment of an illuminating device according to the present invention.

FIG. 4 schematically shows as an example another illuminating device 10 according to the present invention. It is based, in principle, on the embodiment as shown in FIGS. 1 through 3. However, two additional light modules 20a and 20b are additionally provided as satellites, which can be preferably controlled separately. In particular, they can be moved, preferably by means of a motor, in terms of their illumination direction. The method for the illuminating device 10 according to this embodiment functions in exactly the same manner as was explained with reference to FIGS. 1 through 3.

Figure 5A:
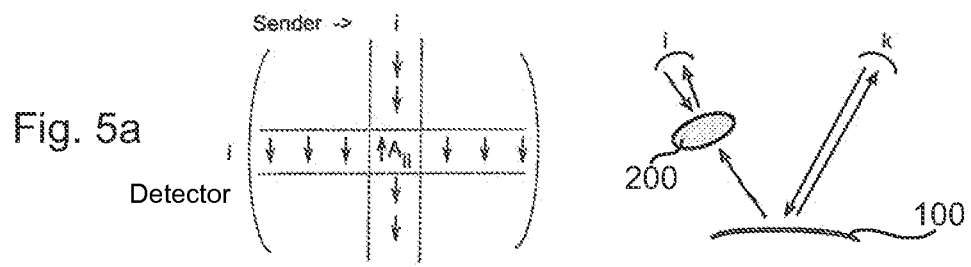
FIG. 5a is a schematic view of the analysis with a first blocking object.
Figure 5B:
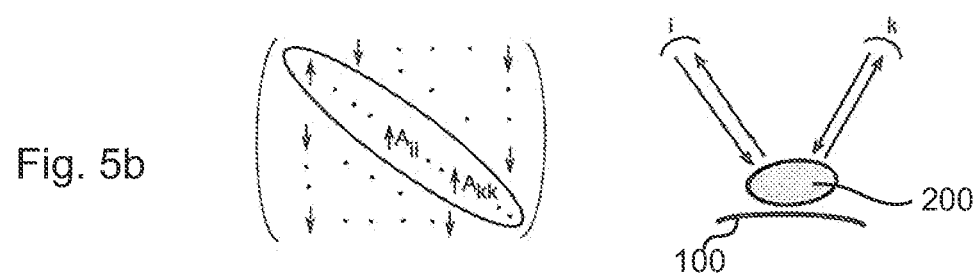
FIG. 5b is a schematic view of an analysis with another blocking object.

FIGS. 5a and 5b schematically show a possibility of analysis in a method according to the present invention. FIG. 5a shows the situation that is basically also shown in FIG. 3. An illuminated area 100 is illuminated by an illuminating device 10 (not shown), and two detectors I and k can be recognized. The object 200 is located in the area of the light module I, so that there is an increased reflection there. A characteristic amplitude distribution can correspondingly be recognized in a detection matrix as it is shown in the left-hand part of FIG. 5a for this detector with respect to the characteristic light type of the light module I. The object 200 is in another position in FIG. 5b, so that the reflection situation and hence the detection situation change as well. This leads to a change in the amplitudes and hence to a change in the detection matrix, as this is likewise shown in the left-hand part of FIG. 5b. An especially unambiguous and accurate assignment of the object 200 to the corresponding light modules 20 will correspondingly become possible due to a corresponding analysis of the detection matrices shown. In particular, it becomes possible to bring about an especially advantageous improvement of the illumination of the illuminated area by correspondingly regulating the light intensity of the individual light modules 20 regardless of the number of objects and the accurate position of the objects.

Figure 6A:
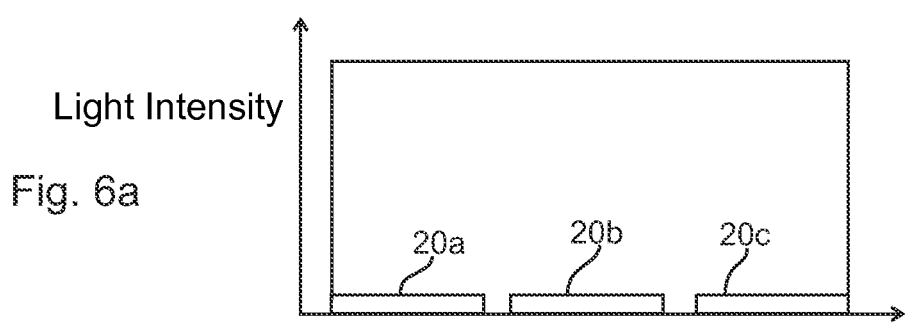
FIG. 6a is a schematic view of the light intensity of a plurality of light modules without blocking object.
Figure 6B:
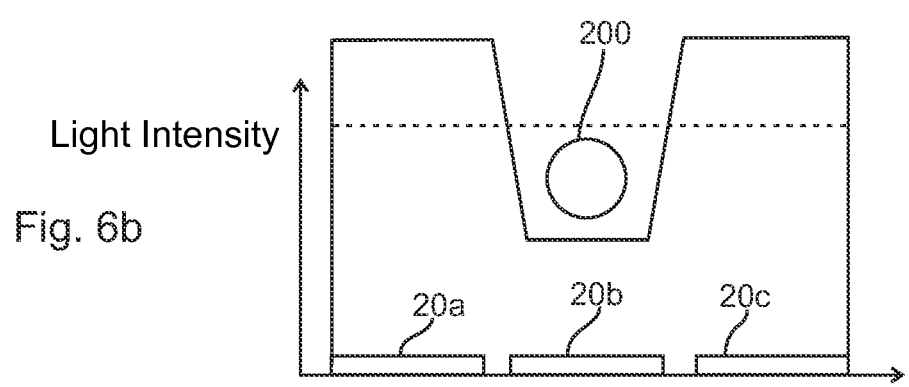
FIG. 6b is the view according to FIG. 6a with blocking object.

FIGS. 6a and 6b show a basic possibility of regulating the light intensity. Thus, FIG. 6a shows the arrangement of three light modules 20*a*, 20*b* and 20*c* next to each other. If there is no object 200 in a blocking position, the same light intensity can be used for all light modules 20*a*, 20*b* and 20*c* of this embodiment. If an object 200 is moved now into a blocking position, as this is shown in FIG. 6*b*, this object is in a blocking position relative to the middle light module 20*b*. The original light intensity is indicated by a broken line, as it was shown in FIG. 6*a*. The light module 20*b* is now recognized as a blocked light module 20 due to the blocking situation of the object 200. The light intensity of the adjacent light modules 20*a* and 20*c* is correspondingly increased or, as an alternative, the light intensity of the blocked light module 20*b* is reduced to improve the illumination. Besides a reduction of the probability of blinding for the surgeon, an improvement of illumination is achieved, because radiation is quasi emitted around the object 200 by the adjacent light modules 20*a* and 20*c* and the casting of a shadow is avoided or reduced.

The above explanation of the embodiments describes the present invention only in connection with examples. Individual features of the embodiments, insofar as technically meaningful, may, of course, be freely combined with one another without going beyond the scope of the present invention.

While specific embodiments of the invention have been shown and described in detail to illustrate the application of the principles of the invention, it will be understood that the invention may be embodied otherwise without departing from such principles.

The invention claimed is:

1. A method for improving the illumination of an illuminated area of an illuminating device with at least two light modules, the method comprising the steps of:
    emitting a characteristic light type of the light module with a preset light amplitude setting for each light module, wherein each light module has an LED as a characteristic illuminant, which emits the characteristic light type, and wherein the characteristic light type is generated by pulse width modulation, wherein a pulse width modulation characteristic parameter of the pulse width modulation of the characteristic light type of each of the at least two light modules is different from a pulse width modulation characteristic parameter of the pulse width modulation of the characteristic light type of each other of the at least two light modules to provide each of the at least two light modules with a different characteristic light type unambiguously assigned to the corresponding light module;
    detecting reflected light of all characteristic light types and amplitudes of each of the different characteristic light types unambiguously assigned to the corresponding light modules, to identify detected light module light amplitudes of each of the light modules;
    comparing the detected light module light amplitudes; and
    varying a light intensity of at least one light module on the basis of the comparing of the detected light module light amplitudes.

2. A method in accordance with claim 1, wherein the detection of the reflected amplitudes of all characteristic light types is carried out in at least two different light detection positions.

3. A method in accordance with claim 1, wherein the detection of the reflected amplitudes of all characteristic light types is carried out in at least two light modules.

4. A method in accordance with claim 1, wherein a local blocking of the illuminated area is assigned, as an assigned blocking to a light module, by comparison of the detected amplitudes for each light module, based on the characteristic of the pulse width modulation of the characteristic light type.

5. A method in accordance with claim 4, wherein the light intensity of at least one light module, which is arranged adjacent to the light module with the assigned blocking, is increased and/or the light intensity of the light module with the assigned blocking is reduced.

6. A method in accordance with claim 1, wherein the characteristic light type has a wavelength in the range of 6 μm to 200 nm.

7. A method in accordance with claim 1, wherein the characteristic of the pulse width modulation of the characteristic light types have a sinusoidal modulation, and a phase of the sinusoidal modulation is shifted from one light module to the next.

8. A method in accordance with claim 1, wherein;
    frequency of modulation is used as a characteristic parameter in order to make possible an unambiguous assignment to the corresponding light module; and
    the comparison of the detected amplitudes for each light module is performed several times and the results over time are compared with one another.

9. A method according to claim 1, further comprising the steps of:
    providing an operating room;
    positioning the illuminating device with the at least two light modules in the operating room; and
    carrying out the steps of emitting, detecting comparing and varying with the illuminating device in the operating room.

10. An illuminating device for the illumination of an illuminated area, the illuminating device comprising:
    at least two light modules with at least one illuminant each and with at least one characteristic light emitting diode (LED) illuminant for the emission of a characteristic light type generated by pulse width modulation, wherein a pulse width modulation characteristic parameter of the pulse width modulation of the characteristic light type of each of the at least two light modules is different from a pulse width modulation characteristic parameter of the pulse width modulation of the characteristic light type of each of the other at least two light modules with each characteristic light type being identifiably different from each other characteristic light type based on the different pulse width modulation characteristic parameters and being unambiguously assigned a corresponding one of the at least two light modules;
    at least one detector for the detection of reflected light of all of the characteristic light types and detection of amplitudes of each of the characteristic light types, to identify light module light amplitudes of the particular light modules; and
    at least one computer configured for a comparison of the detected light module light amplitudes.

11. An illuminating device in accordance with claim 10, wherein the computer is configured, further, for varying the light intensity of at least one of the light modules on the basis of the comparison of the detected amplitudes of characteristic light types for each light module.

12. An illuminating device in accordance with claim 11, wherein the computer is configured to:
    control the emission of the characteristic light type of the light module with a preset amplitude from each light module, wherein each light module has an LED as a characteristic illuminant, which emits the characteristic light type, and wherein the characteristic light type is generated by pulse width modulation, wherein a characteristic of the pulse width modulation of the characteristic light type of each of the at least two light modules is different from a characteristic of the pulse width modulation of the characteristic light type of each other of the at least two light modules;

control the detection of the reflected light of all characteristic light types that identify the light module light amplitudes of the particular light modules;

control a comparison of the detected light module light amplitudes; and control the variation of the light intensity of at least one light module on the basis of the comparison of the detected light module light amplitudes, wherein:

the detection of the reflected amplitudes of all characteristic light types is carried out in at least one of two or more different light detection positions and with two or more detectors of reflected light.

13. An illuminating device in accordance with claim 10, wherein:

at least two detectors are provided, which are arranged in each of the light modules; and frequency of modulation is used as a characteristic parameter in order to make possible an unambiguous assignment to the corresponding light module.

14. A method for improving the illumination of an illuminated area, the method comprising the steps of:

providing an illuminating device for the illumination of the illuminated area the illuminating device comprising:

at least two light modules with at least one illuminant each and with at least one characteristic light emitting diode (LED) illuminant for the emission of a characteristic light type generated by pulse width modulation to provide each of the light modules with a different characteristic light type, wherein a pulse width modulation characteristic parameter of the pulse width modulation of the characteristic light type of each of the at least two light modules is different from a pulse width modulation characteristic parameter of the pulse width modulation of the characteristic light type of each other of the at least two light modules providing each characteristic light type with an identification code unambiguously assigning each characteristic light type to a corresponding one of the at least two light modules;

at least one detector for the detection of the amplitudes of reflected light of each of the different characteristic light types; and at least one computer configured for a comparison of the detected amplitudes of each of the different characteristic light types;

emitting the characteristic light with the light emitting diode (LED) illuminant;

detecting reflected light of each of the different characteristic light types with the at least one detector to provide detected amplitudes of each of the different characteristic light types that are detected light module light amplitudes of reflected light of the particular light modules;

comparing the detected light module light amplitudes; and varying the light intensity of at least one light module on the basis of the comparing of detected light module light amplitudes.

15. A method in accordance with claim 14, the detection of the reflected light of all characteristic light types is carried out in at least one of two or more different reflected light detection positions of the light modules and with two or more detectors of amplitudes of reflected light.

16. A method in accordance with claim 15, wherein a local blocking of the illuminated area is assigned, as an assigned blocking to a light module by comparison of the detected amplitudes for each light module, based on the characteristic of the pulse width modulation of the characteristic light type.

17. A method in accordance with claim 16, wherein the light intensity of at least one light module, which is arranged adjacent to the light module with the assigned blocking, is increased and/or the light intensity of the light module with the assigned blocking is reduced.

18. A method in accordance with claim 14, wherein the computer is configured to:

control the emission of the characteristic light type of the light module with a preset amplitude from each light module, wherein each light module has an LED as a characteristic illuminant, which emits the characteristic light type, and wherein the characteristic light type is generated by pulse width modulation, wherein a characteristic of the pulse width modulation of the characteristic light type of each of the at least two light modules is different from a characteristic of the pulse width modulation of the characteristic light type of each other of the at least two light modules;

control the detection of the reflected light of all characteristic light types that are the detected light module light amplitudes of the particular light modules;

control a comparison of the detected light module light amplitudes; and control the variation of the light intensity of at least one light module on the basis of the detected light module light amplitudes, wherein:

the detection of the reflected light of all characteristic light types is carried out in at least one of two or more different light detection positions and with two or more detectors of the amplitudes of reflected light of all characteristic light types.

19. A method in accordance with claim 14, wherein:

the characteristic light type has a wavelength in the range of 6 μm to 200 nm; and the pulse width modulation characteristic of the characteristic light types is based on a sinusoidal modulation, and the phase of the sinusoidal modulation is shifted from one light module to the next.

20. A method in accordance with claim 14, wherein:

frequency of modulation is used as a characteristic parameter in order to make possible an unambiguous recognition of light from the corresponding light module; and the comparison of the detected amplitudes for each light module is performed several times and the results over time are likewise compared with one another.

* * * * *